(12) United States Patent
Hovekamp

(10) Patent No.: US 11,826,183 B1
(45) Date of Patent: Nov. 28, 2023

(54) SPECIMEN BAG HOLDER

(71) Applicant: Jennifer Sage Hovekamp, San Ramon, CA (US)

(72) Inventor: Jennifer Sage Hovekamp, San Ramon, CA (US)

( * ) Notice: Subject to any disclaimer, the term of this patent is extended or adjusted under 35 U.S.C. 154(b) by 0 days.

(21) Appl. No.: 17/737,022

(22) Filed: May 5, 2022

(51) Int. Cl.
 *A47F 5/08* (2006.01)
 *A61B 50/22* (2016.01)
 *A61B 50/30* (2016.01)

(52) U.S. Cl.
 CPC ............... *A61B 50/22* (2016.02); *A47F 5/08* (2013.01); *A61B 50/30* (2016.02)

(58) Field of Classification Search
 CPC ......... A61B 50/22; A61B 50/30; A61B 50/36; A61B 50/37; A47F 5/0006; A47F 5/0884; A47F 7/0042; A47F 13/085; A47F 9/042; A47F 5/08; A47B 95/008; A47G 23/0258
 USPC ..... 211/85.15, 85.17, 119.004, 88.01, 94.01, 211/12; 248/690, 692, 301, 220.22, 248/220.21, 223.31, 95
 See application file for complete search history.

(56) References Cited

U.S. PATENT DOCUMENTS

| | | | | | |
|---|---|---|---|---|---|
| 1,446,036 | A | * | 2/1923 | Dodd | A47F 5/08 |
| | | | | | 248/312.1 |
| 2,580,099 | A | * | 12/1951 | Jaeger | B25H 3/04 |
| | | | | | 211/DIG. 1 |
| 2,639,040 | A | * | 5/1953 | Tapley | A47F 5/0068 |
| | | | | | 211/119.003 |
| 3,693,923 | A | * | 9/1972 | Ayoub | A47K 5/04 |
| | | | | | 248/309.2 |
| 3,794,285 | A | * | 2/1974 | Barts | A47K 5/12 |
| | | | | | 211/72 |
| 4,165,852 | A | * | 8/1979 | Chervenak | F16M 11/045 |
| | | | | | 248/225.11 |
| 4,215,840 | A | * | 8/1980 | Babberl | G09F 1/10 |
| | | | | | 248/220.22 |
| 4,784,360 | A | * | 11/1988 | Mok | B60N 3/101 |
| | | | | | 248/311.2 |
| 4,798,170 | A | * | 1/1989 | DePiazzy | A01K 1/0356 |
| | | | | | 119/61.57 |
| 4,828,121 | A | * | 5/1989 | Willcocks, Jr. | A47F 5/0068 |
| | | | | | D6/567 |
| 4,843,977 | A | * | 7/1989 | Bridges | A47B 96/061 |
| | | | | | 211/90.01 |
| 4,898,354 | A | * | 2/1990 | Whittington | A47B 57/585 |
| | | | | | 211/175 |
| 4,909,464 | A | * | 3/1990 | Levine | G09F 7/22 |
| | | | | | 40/606.15 |

(Continued)

OTHER PUBLICATIONS

Anonymous. "Biohazard Bag Holder." Printed Sep. 29, 2021. 2 pages. Published by Thomas Scientific. https://www.thomassci.com/Equipment/Dispensers/_/Biohazard-Bag-Holder.

(Continued)

*Primary Examiner* — Jennifer E. Novosad
(74) *Attorney, Agent, or Firm* — Heather Johnston; Prasant Muralidhar

(57) ABSTRACT

An apparatus may include a rigid body. The rigid body may include a top portion with a holding component, a middle portion connected to the top portion, and a bottom portion connected to the top portion via the middle portion. The apparatus may include a stabilizing unit connected to the rigid body and a mounting unit connected to the rigid body.

14 Claims, 5 Drawing Sheets

(56) References Cited

U.S. PATENT DOCUMENTS

| | | | | | |
|---|---|---|---|---|---|
| 4,960,257 | A * | 10/1990 | Waters | ............... | G06F 1/1611 248/442.2 |
| 5,054,672 | A * | 10/1991 | Weissman | ............... | A45F 5/02 224/678 |
| 5,224,609 | A * | 7/1993 | Bauer | ............... | A47F 7/0021 211/70.6 |
| 5,288,050 | A * | 2/1994 | Armstrong | ............ | F16M 11/08 248/479 |
| 5,425,461 | A * | 6/1995 | Larson | ............... | A47F 5/0838 211/88.01 |
| 5,472,167 | A * | 12/1995 | Shillington | .......... | A47F 5/0861 248/552 |
| 5,639,060 | A * | 6/1997 | Spoonts | ............ | F16M 13/022 211/88.01 |
| 5,806,692 | A * | 9/1998 | Pepper | ............... | A47B 96/027 211/70.1 |
| 5,870,969 | A * | 2/1999 | Boyce | ............... | A01K 5/0114 119/51.5 |
| 6,045,097 | A * | 4/2000 | Gaffar | ............ | A61J 1/16 211/85.15 |
| 6,065,728 | A * | 5/2000 | Spradlin | ........... | G06K 7/10861 248/300 |
| 6,340,145 | B1 * | 1/2002 | Tagami | ............... | F16M 13/022 108/26 |
| 6,357,713 | B1 * | 3/2002 | BeBow | ............... | F16M 11/041 248/312.1 |
| 6,533,128 | B1 * | 3/2003 | Beneway | ............ | G11B 33/0411 312/9.11 |
| 7,341,231 | B2 * | 3/2008 | Zarn | ............... | F16M 13/022 403/294 |
| 7,395,842 | B2 * | 7/2008 | Dyer | ............... | B65B 67/12 211/85.15 |
| 7,434,699 | B2 * | 10/2008 | Stukenberg | ......... | A47G 1/1646 211/87.01 |
| 7,784,625 | B2 * | 8/2010 | Burgess | ............. | A47B 46/005 211/85.15 |
| 7,798,336 | B2 * | 9/2010 | Shiao | ............... | B25H 3/04 211/DIG. 1 |
| 7,802,763 | B2 * | 9/2010 | Faller | ............... | A47J 47/01 141/10 |
| 7,837,165 | B2 * | 11/2010 | Stone | ............... | F16M 13/02 248/220.21 |
| 8,070,378 | B2 * | 12/2011 | Gargaro, III | .......... | A01K 97/10 248/225.11 |
| 8,196,775 | B1 * | 6/2012 | Ballesteros | ............ | A61B 50/20 211/90.04 |
| 8,245,992 | B2 * | 8/2012 | Matsui | ............... | F16M 13/02 248/224.51 |
| 8,297,571 | B2 * | 10/2012 | Xue | ............... | F16M 11/10 248/220.22 |
| 8,651,290 | B1 * | 2/2014 | Fonseca | ............ | A47F 7/0035 211/65 |
| 9,004,433 | B2 * | 4/2015 | Krieger | ............... | B60N 3/102 224/276 |
| 10,412,929 | B2 * | 9/2019 | Kasper | ............... | A01K 5/0114 |
| 2004/0118986 | A1 * | 6/2004 | Will | ............... | B25H 3/04 248/220.22 |
| 2006/0180561 | A1 * | 8/2006 | Wisnoski | ............ | A47F 5/0846 211/94.01 |
| 2007/0278167 | A1 * | 12/2007 | Robertson | ........... | A47B 96/02 211/88.01 |
| 2017/0143121 | A1 * | 5/2017 | Grice | ............... | A47B 96/068 |
| 2020/0221871 | A1 * | 7/2020 | Sisto | ............... | A47B 96/028 |

OTHER PUBLICATIONS

Anonymous. "Scienceware® Polygrid® Bag Holders." Printed Sep. 29, 2021. 3 pages. Published by Thomas Scientific. https://www.thomassci.com/Covid-19/Sample-Collection-Supplies/Sample-Transport-Bags/_/POLYGRID-BAG-HOLDERS.

Anonymous. "Clavies® Biohazard Bag Holders." Printed Sep. 29, 2021. 2 pages. Published by Thomas Scientific. https://www.thomassci.com/Covid-19/Sample-Collection-Supplies/Sample-Transport-Bags/_/Clavies-Biohazard-Bag-Holders.

Anonymous. "Scienceware® Poxygrid® Bench-Top Biohazard Bag Holder Kit." Printed Sep. 29, 2021. 3 pages. Published by Thomas Scientific. https://www.thomassci.com/Laboratory-Supplies/Bags/_/AUTOCLAVABLE-BIOHAZARD-BAG-AND-HOLDER.

Anonymous. "Metro® Storage Flexline Specimen Bag Holder Metro FL575." Printed Sep. 29, 2021. 2 pages. Published by Safety Supply America, Inc. https://www.metroshelvesusa.com/product/1059/metro-storage-flexline-specimen-bag-holder-metro-fl575.

* cited by examiner

SPECIMEN BAG HOLDER

BACKGROUND

The present disclosure relates to sample collection and, more specifically, to sanitary specimen collection.

A specimen may be collected for testing. A specimen collector may collect a specimen. The specimen collector may use a specimen collection receptacle (e.g., a specimen bag) to retrieve and/or transport a specimen for testing. In a hospital or similar patient setting, the specimen collector may enter a patient room with a specimen collection receptacle to retrieve the specimen.

SUMMARY

Embodiments of the present disclosure include an apparatus and a method for collecting a specimen. The apparatus may include a rigid body. The rigid body may include a top portion with a holding component, a middle portion connected to the top portion, and a bottom portion connected to the top portion via the middle portion. The apparatus may include a stabilizing unit connected to the rigid body and a mounting unit connected to the rigid body.

The above summary is neither intended to describe each embodiment of the present disclosure nor is it intended to describe every implementation of the present disclosure.

BRIEF DESCRIPTION

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
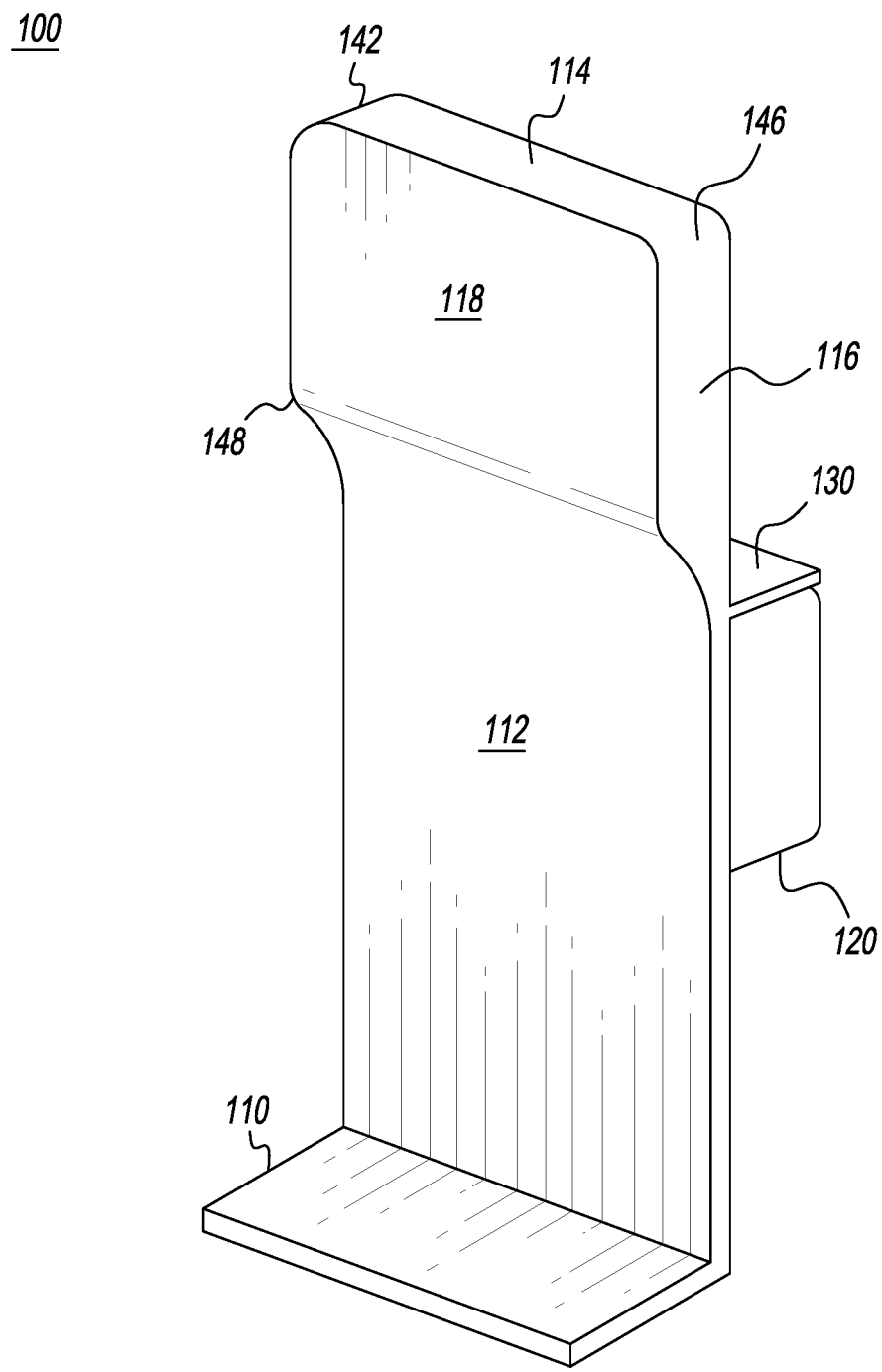
FIG. 1 illustrates a front view of a specimen bag holder in accordance with some embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to sample collection and, more specifically, to sanitary specimen collection.

A nurse or other specimen collector may need to obtain a specimen to submit the specimen to a laboratory for testing and/or analysis. Collecting a specimen may be a messy process, and some of a collected specimen may end up outside of the intended specimen bag or other collection receptacle. A specimen may be saliva, blood, urine, semen, wound drainage, other bodily fluid, fecal matter, or other sample which may be unsanitary or otherwise undesirable to come into contact with.

A specimen collector may generally be in a sterile and/or otherwise clean environment. Such an environment may be, for example, a hospital campus, a hospital building, a nursing facility, an outpatient facility, a therapy space, a laboratory, a wing of a hospital building or nursing facility, a patient room, an operating room, or a similar location. It may be desirable to maintain the cleanliness of one or more of these environments during specimen collection and/or transportation of the specimen sample. However, a patient room may be unsupervised such that a surface within the patient room may contaminate a specimen bag such that a test may return an erroneous result and/or a specimen collector such that the specimen collector may contract an illness as a result of contacting the specimen. To comply with various guidelines, rules, regulations, and standards for maintaining a sterile environment, specimen collectors may put themselves at risk of contamination.

For example, certain standards require specimen collectors in hospitals to don gloves for specimen collection and remove gloves before exiting the collection room. Part of the collected sample may contact the outside of the specimen bag during the collection process; the specimen collector must then choose between sterile environment standards (e.g., the standards set by hospital accreditation organizations) and their personal safety (e.g., self-contamination). Specifically, by complying with standards that require the removal of gloves before exiting the room of collection, the specimen collector risks self-contamination to transport the specimen bag to the laboratory for testing. Alternatively, the specimen collector may opt to continue using their gloves outside of the collection room, risking the accreditation of the hospital.

Preventing contact with a specimen may both increase compliance with sanitary standards and reduce or even eliminate the risk of contamination of a specimen collector. Additionally, reducing and/or eliminating contamination risk of a specimen collector reduces the risk of other environments being contaminated. For example, if a specimen collector is contaminated, the specimen collector may contaminate other locations such as the laboratory and the hallways between the collection site and the laboratory; however, if the specimen collector is not contaminated, then the specimen collector is less likely to spread the contamination. Therefore, the contamination of the other environments the specimen collector contacts may be reduced by reducing the likelihood of contamination of the specimen collector.

The present disclosure includes a device to hold open a specimen bag during specimen collection. A device in accordance with the present disclosure may enable the hanging of a specimen bag to maintain an open posture of the specimen bag such that a specimen collector may deposit a specimen in the specimen bag without requiring the specimen collector to contact the outside of the specimen bag. In some embodiments, a device in accordance with the present disclosure may enable maintaining sanitization of one or more external surfaces of a specimen bag. In some embodiments, the device may enable a specimen collector to deposit a messy specimen into a specimen bag without contamination of the outside of the specimen bag.

An apparatus in accordance with some embodiments of the present disclosure may include a rigid body. The rigid body may include a top portion, a middle portion connected to the top portion, and a bottom portion connected to the top portion via the middle portion. The top portion may have a holding portion. The apparatus may include a stabilizing unit connected to the rigid body and a mounting unit connected to the rigid body.

In some embodiments of the present disclosure, the mounting unit may be connected to the middle portion of the rigid body.

In some embodiments of the present disclosure, the mounting unit has a mounting unit surface area and a mounting unit width approximately perpendicular thereto. The mounting unit surface area may be aligned adjacent a body mounting surface area on the rigid body, and the mounting unit width separates the rigid body from an external surface.

In some embodiments of the present disclosure, the apparatus may further include a protrusion extending from the rigid body, and the mounting unit may connect to the rigid body at the protrusion. In some embodiments, the stabilizing unit may extend from the rigid body in a first direction and the protrusion extends from the rigid body in a second direction.

In some embodiments of the present disclosure, the apparatus may further include a rigid body surface area defined by a rigid body height and a rigid body width. The rigid body surface area may be substantially vertical. The rigid body surface area may include a top portion surface area of the top portion, a middle portion surface area of the middle portion, and a bottom surface area of the bottom portion. In some embodiments of the present disclosure, the apparatus may further include a top portion depth perpendicular to the rigid body surface area and a bottom portion depth perpendicular to the rigid body surface area; the top portion depth may be greater than the bottom portion depth.

In some embodiments, the holding component may be designed to enable attachment and/or detachment of a held unit. The holding component may be, in whole or in part, a result of the top portion depth variance. The holding component may include a deep upper cusp to discourage the held unit from slipping from said holding component and one or more curved edges to enable easy attachment and/or detachment of the held unit. The held unit may be, for example, a bag (e.g., a specimen bag).

In some embodiments of the present disclosure, the mounting unit may mount to an external surface. In some embodiments, the external surface may be a vertical surface approximately parallel to gravitational forces; a vertical surface may be, for example, a wall or a side of a piece of furniture.

In some embodiments of the present disclosure, the mounting unit may further include a detachable connector. The detachable connector may be any mechanism for connecting the mounting unit to something else without causing substantial damage to the mounting unit. For example, the detachable connector may be a screw, a nut and a bolt, a nail, a set of screws, a set of nuts and bolts, a set of nails, or other detachable connector or set thereof.

In some embodiments, the detachable connector may have a connecting component (e.g., a screw) and a receiving component (e.g., a premade hole for the screw). In some embodiments, the mounting unit may be a wooden mounting block and the receiving component may be a hole coated in a material to enable repeated attachment and detachment of the wooden mounting block while preventing the splitting of the wooden mounting block which may result from repetitive attachment/detachment stress. In some embodiments, the detachable connector may detachably connect the mounting unit to an external surface. In some embodiments, the detachable connector may detachably connect the mounting unit to the rigid body.

In some embodiments of the present disclosure, the apparatus may further include a contiguous material constituting the rigid body and the stabilizing unit. For example, the top portion, the middle portion, and the bottom portion may be one contiguous material such as plastic, wood, metal, or other material. In some embodiments, the contiguous material may include the stabilizing unit such that the top portion, middle portion, bottom portion, and stabilizing unit are contiguous. In some embodiments, the contiguous material may include the protrusion such that the top portion, middle portion, bottom portion, stabilizing unit, and the protrusion are contiguous.

In some embodiments of the present disclosure, the apparatus may have collection side and a mounting side. The mounting unit may attach to the mounting side. In some embodiments, a first ledge may protrude from the mounting side of the middle portion of the device; the mounting unit may connect thereto. In some embodiments, a second ledge may protrude from the bottom portion of the device; the second ledge may protrude from just the collection side, just the mounting side, or both.

A method in accordance with some embodiments of the present disclosure may include obtaining a specimen collection device, attaching a specimen receptacle to the specimen collection device, and depositing a specimen into the specimen receptacle. The specimen collection device may include a rigid body. The rigid body may include a top portion with a holding component, a middle portion connected to the top portion, and a bottom portion connected to the top portion via the middle portion. The apparatus may include a stabilizing unit connected to the rigid body and a mounting unit connected to the rigid body.

The figures explain various embodiments and principles of the disclosure; the figures are not intended to describe every implementation of the present disclosure.

In some embodiments, a device in accordance with the present disclosure may hold open a bag such that a sample may be deposited in the bag by a sample collector without the sample collector touching the outside of the bag after contacting the sample. A sample may be, for example, a medical specimen (e.g., fecal matter destined for laboratory testing), a ground sample (e.g., dirt to be tested for the suitability of growing a certain plant), food to be stored (e.g., for meal planning), or some other material.

A ledge may extend from the front of the bottom of the device to support the weight of a sample; such a ledge may be referred to as a stabilizer, stabilizing portion, bottom ledge, or similar term. Another ledge may protrude from the back of the middle of the device to mount the device on an external surface (e.g., a wall); such a ledge may be referred to as a protrusion, connector ledge, protruding ledge, or the like. In some embodiments, the protrusion may extend from an upper or lower portion of the device. The device may mount to an external surface (e.g., a wall) via a mounting unit such that the main body and/or the protrusion protruding from the back of the device connects to the mounting unit which connects to the external surface.

A specimen collector may use a device in accordance with the present disclosure by obtaining a specimen bag, opening the specimen bag, attaching the specimen bag to a top part of the specimen bag holder, donning gloves, collecting a specimen, depositing the specimen in the open specimen bag without contacting an external surface of the bag, doffing the gloves, and collecting the specimen bag from the specimen bag holder.

In some embodiments, the specimen collector may cleanse their hands between doffing the gloves and collecting the specimen bag. In some embodiments, the specimen bag may be sealed after retrieval from the specimen bag holder. In some embodiments, the specimen collector may only touch the outside of the specimen bag with ungloved, clean hands.

FIG. 1 illustrates a front view of a specimen bag holder 100 in accordance with some embodiments of the present disclosure. The specimen bag holder 100 may have a top portion 118 and a main body 112.

The top portion 118 may include a top edge 114 and top corners 142 and 146. In some embodiments, the top corners 142 and 146 may be rounded. Rounding the top corners 142 and 146 may, for example, enhance the ability of an individual (e.g., a specimen collector such as a nurse) to quickly and easily attach a specimen bag to the specimen bag holder 100.

The specimen bag holder 100 may have a main body 112, a stabilizing portion 110, and a protrusion 130. The stabilizing portion 110 may extend away from the main body 112 at the bottom of the main body 112. The stabilizing portion 110 may extend in a collection direction (e.g., where the receiving portion of a specimen bag will be when hanging from the specimen bag holder 100). The stabilizing portion 110 may, for example, extend under a specimen bag while the specimen bag holder 100 is supporting the specimen bag.

A mounting unit 120 may be attached to the main body 112. The mounting unit 120 may be attached on a mounting side of the main body 112 which may be opposite the collection side of the main body 112. The mounting unit 120 may be, for example, a mounting block (e.g., a generally solid material such as a wood block) or a mounting box (e.g., a rigid outside with an empty center portion). The mounting unit 120 may be removable from the specimen bag holder 110 or it may be a contiguous part thereof.

In some embodiments, the mounting unit 120 may be attached directly to the main body 112. In some embodiments, the mounting unit 120 may be attached directly to the protrusion 130. In some embodiments, the mounting unit 120 may be attached directly to both the main body 112 and the protrusion 130. In some embodiments, the mounting unit 120 may be attached (permanently or detachably) to an external surface (e.g., a wall) such that the main body 112 and/or the protrusion 130 may attach to the external surface by engaging with the mounting unit 120; engagement may be by, for example, sliding interlocking rails on the main body 112 into matching interlocking rails on the mounting unit 120.

The specimen bag holder 100 may have a height that may be measured vertically or in a y-direction (e.g., from the lowest point of the main body 112 to the highest point of the top edge 114), a width that may be measured horizontally or in an x-direction (e.g., from the left side of the top portion 118 to a right side 116 of the top portion 118), and a depth that may be measured in a z-direction (e.g., from the front of the top portion 118 to the back of the top portion 118). In some embodiments, the height, width, and/or depth may vary depending on where the measurement is taken. For example, the height of the specimen bag holder 100 may be the same on the right side and the left side and have a concavity connecting the two sides. In another example, the top portion 118 may have one width whereas the main body 112 has another width. In a similar example, the top portion 118 may be one inch in depth whereas the main body 112 is one-half inch in depth.

The specimen bag holder 100 may have a curve 148 connecting the top portion 118 with the main body 112 such that the top portion 118 has a depth greater than the depth of the main portion 112. In FIG. 1, the curve 148 is depicted as narrowing the depth of the specimen bag holder 100 such that the right side 116 has a larger depth measurement in the top portion 118 than in the main body 112 segment. In some embodiments, the right side 116 (and/or a left side, not shown) may have a steady depth measurement such that the top portion 118 may be or include a wire that folds out at the top (e.g., ends in a substantially flat platform) and/or curls in on itself (e.g., that the curve 148 is a front portion of the wire connecting with a back portion).

Figure 2:
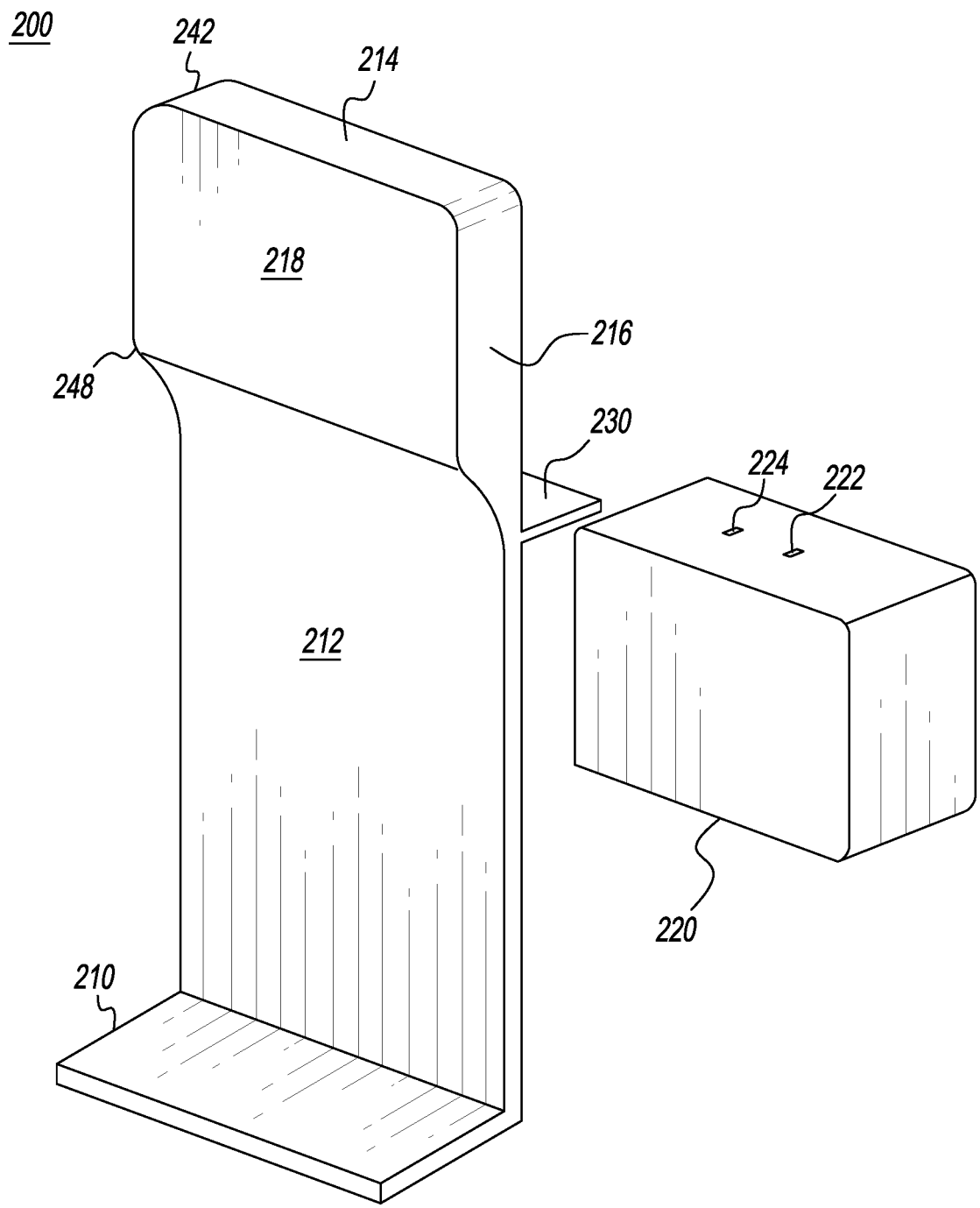
FIG. 2 depicts an exploded view of a specimen bag holder in accordance with some embodiments of the present disclosure.

FIG. 2 depicts an exploded view of a specimen bag holder 200 in accordance with some embodiments of the present disclosure. The specimen bag holder 200 may have a top portion 218, a main body 212, and a mounting unit 220.

The top portion 218 may include a top edge 214 and one or more top corners 242. The specimen bag holder 200 may include a main body 212, a stabilizing portion 210, a mounting unit 220, and a protrusion 230. The specimen bag holder 200 may have multiple sides including, for example, a front (e.g., a specimen collection side), a back (e.g., a mounting side), a left side, and a right side 216.

The mounting unit 220 may include one or more mechanisms for detachably connecting to the main body 212, the protrusion 230, an external surface (e.g., a wall, object, or piece of furniture), or some combination thereof. The mounting unit 220 may include, for example, screw holes 222 and 224 such that screws may be placed through screw holes (not shown) in the protrusion 230 and continue into the screw holes 222 and 224 in the mounting unit 220 to connect the protrusion 230 directly to the mounting unit 220. In some embodiments, the mounting unit 220 may be attached (permanently or detachably) to an external surface (e.g., a wall) such that connecting the protrusion 230 to the mounting unit 220 connects the specimen bag holder 200 to the external surface.

Figure 3:
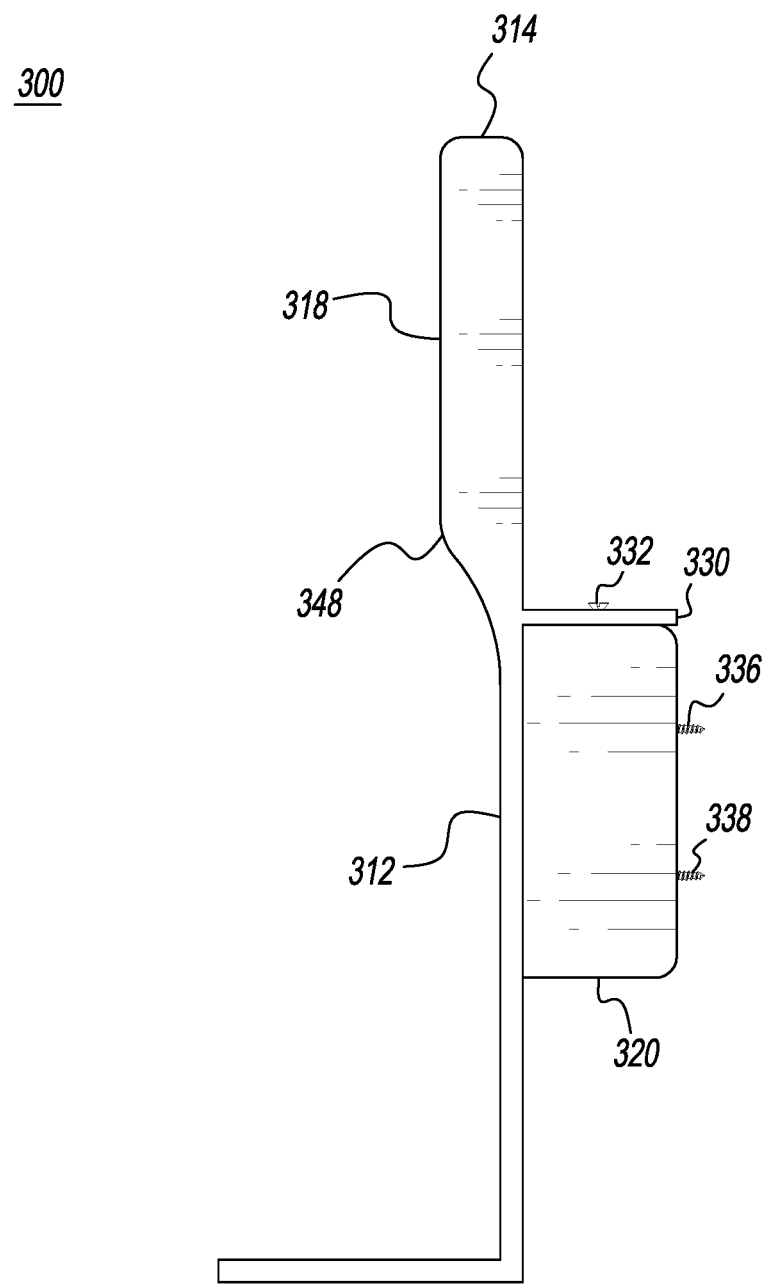
FIG. 3 illustrates a side view of a specimen bag holder in accordance with some embodiments of the present disclosure.

FIG. 3 illustrates a side view of a specimen bag holder 300 in accordance with some embodiments of the present disclosure. The specimen bag holder 300 may have a top edge 314, a top portion 318, a main body 312, a curved portion 348 connecting the top portion 118 to the main body 312, a mounting unit 320, and a protrusion 330. The top portion 318 may have rounded corners. The mounting unit 320 may the protrusion 330, the main body 312, and/or an external surface (not shown).

The mounting unit 320 may include one or more mechanisms (e.g., connectors) for detachably connecting to the main body 212, the protrusion 230, an external surface (e.g., a wall, object, or piece of furniture), or some combination thereof. In FIG. 3, the mounting unit 320 is connected to the protrusion 330 via a first screw 332; in some embodiments, a second screw may also be used to connect the mounting unit 320 to the protrusion 330. The mounting unit 320 includes two connectors 336 and 338 for attaching the mounting unit 330 to an external surface (not shown).

In some embodiments, the mounting unit 320 and/or the protrusion 330 will have a depth such that the main body 312 and the top portion 318 of the specimen bag holder 300 may be separated from an external surface. For example, in some embodiments, it may be preferable for the top portion 318 and/or the main body 312 to be separated from a wall by 2-3 inches such that a specimen collector may insert a hand between the top portion 318 and the wall to comfortably hang a specimen bag from the top portion 318 of the specimen bag holder 300; in such embodiments, the protrusion 330 and/or the mounting unit 320 may provide the separation between the top portion 318 and the wall.

In some embodiments, the protrusion 330 may extend beyond the mounting unit 320 such that, for example, the mounting unit 320 is connected directly to the protrusion 330 and there is a space between the mounting unit 320 and the main body 312. In some embodiments, the mounting unit 320 may extend beyond the protrusion 330; the mounting unit 320 may be adjacent the main body 312 and/or top portion 318 and the protrusion 330 extends just far enough to attach to the mounting unit 320 with a screw 332. In some embodiments, the mounting unit 320 may be separated from the main body 312 but adjacent an external surface and the protrusion 330 may connect the mounting unit 320 to the main body 312.

Figure 4:
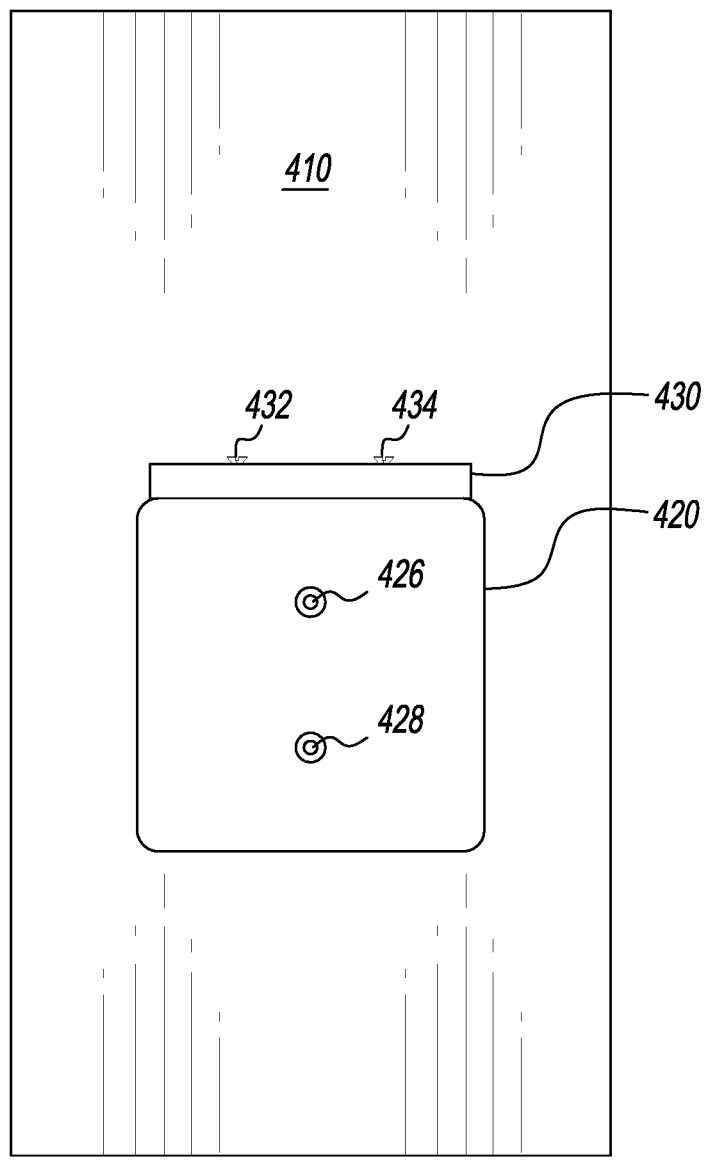
FIG. 4 depicts a rear view of a specimen bag holder in accordance with some embodiments of the present disclosure.

FIG. 4 depicts a rear view of a specimen bag holder 400 in accordance with some embodiments of the present disclosure. The specimen bag holder 400 has a rigid body 410, a protrusion 430, and a mounting unit 420. The rigid body 410 may be constructed of any material that either is substantially rigid (e.g., stainless steel or a firm plastic) or may be made rigid (e.g., a ceramic that may be fired in a furnace to retain its shape).

The mounting unit 420 may be attached to the protrusion 430 with screws 432 and 434. In some embodiments, the mounting unit 420 may be attached to the protrusion 430 and/or the rigid body 410 via other means such as, for example, nails, interlocking rails, hook-and-loop tape, other mechanism, or some combination thereof. In some embodiments, the rigid body 410, the mounting unit 420, and the protrusion 430 may be one contiguous material; for example, the rigid body 410 may have a protrusion 430 that extends from its main body (e.g., the main body 312 shown in FIG. 3) and curves down (e.g., forming a surface approximately parallel to the main body) to form the mounting unit 420 such that the entire specimen bag holder 400 is one contiguous piece of material. In some embodiments, the protrusion 430 may drape over a first external surface (e.g., a railing) such that the mounting unit is positioned between the first external surface and a second external surface (e.g., a wall) and the rigid body 410 is separated from the second external surface.

The mounting unit 420 may have one or more screw holes 426 and 428. The screw holes 426 and 428 may assist in connecting the specimen bag holder 400 to an external surface. In some embodiments, the mounting unit 420 may have additional and/or different placements for connections; for example, nails may be used proximate the four corners of a rectangular mounting unit 420, and/or interlocking rails may extend across the top, middle, and/or bottom of the mounting unit 420 to connect to an external surface.

Figure 5:
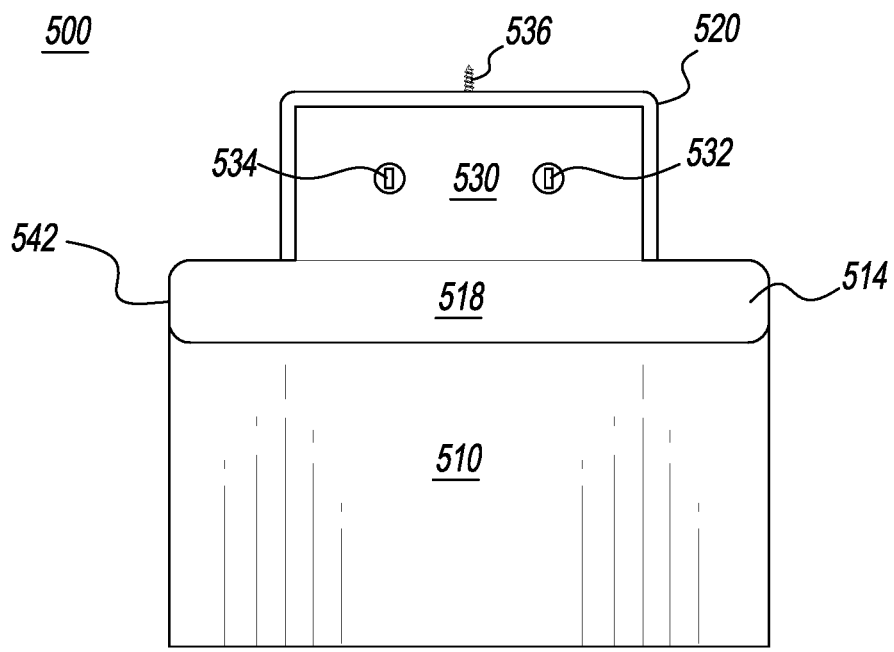
FIG. 5 illustrates a top view of a specimen bag holder in accordance with some embodiments of the present disclosure.

FIG. 5 illustrates a top view of a specimen bag holder 500 in accordance with some embodiments of the present disclosure. The specimen bag holder 500 may have a top edge 514, a top corner 542, a protrusion 530, a mounting unit 520, and a stabilizing portion 510.

The protrusion 530 may connect to the mounting unit 520 with screws 532 and 534. The mounting unit 520 may connect to an external surface (not shown) with a screw 536. In some embodiments, additional and/or alternative connection mechanisms may be used to connect the mounting unit 520 to the protrusion 530 and/or to an external surface. The stabilizing portion 510 may extend from the bottom of a main body of the specimen bag holder 500 (e.g., the bottom of the main body 312 shown in FIG. 3).

Figure 6:
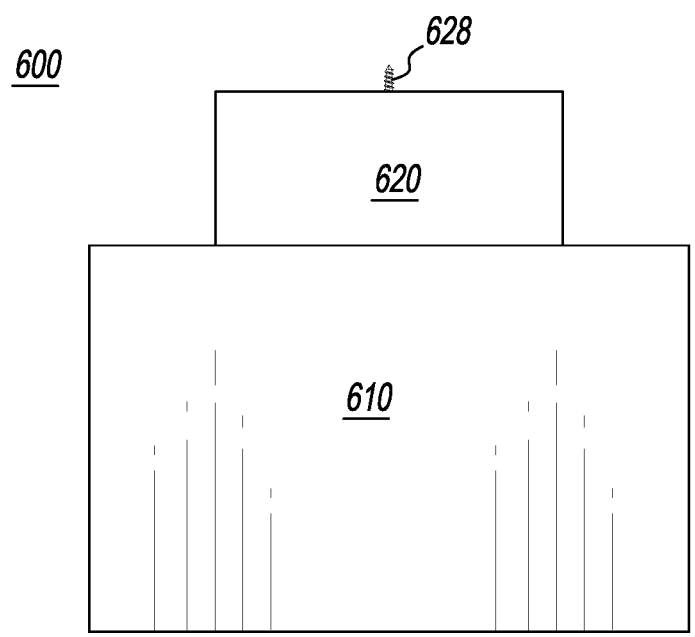
FIG. 6 depicts a bottom view of a specimen bag holder in accordance with some embodiments of the present disclosure.

FIG. 6 depicts a bottom view of a specimen bag holder 600 in accordance with some embodiments of the present disclosure. The specimen bag holder 600 includes a stabilizing portion 610, a mounting unit 620, and a screw 628 for connecting the specimen bag holder 600 to an external surface (not shown). In FIG. 6, the connection mechanism for connecting the specimen bag holder 600 to an external surface is a screw 628 which may be used to attach the mounting unit 620 to an external surface. Other connection mechanisms, detachable or permanent, may be used in accordance with the present disclosure.

Although the present disclosure has been described in terms of specific embodiments, it is anticipated that alterations and modifications thereof will become apparent to the persons of skill in the art. The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or the technical improvement over technologies found in the marketplace or to enable others of ordinary skill in the art to understand the embodiments disclosed herein. Therefore, it is intended that the following claims be interpreted as covering all such alterations and modifications as fall within the spirit and scope of the disclosure.

What is claimed is:

1. A specimen bag holder configured to be attached to an external surface, said holder comprising:
    a rigid body, said rigid body comprising:
        a top portion, wherein said top portion has a holding component for holding a top portion of a specimen bag such that said specimen bag is in an open configuration;
        a middle portion connected to said top portion;
        a protrusion extending from said middle portion in a first direction; and
        a bottom portion connected to said top portion via said middle portion;
    a stabilizing unit connected to said rigid body for supporting a bottom portion of said specimen bag and a weight of contents of said specimen bag, wherein said stabilizing unit extends away from said rigid body in a second direction, wherein said second direction is opposite said first direction and wherein said rigid body and said stabilizing unit are of a contiguous material; and
    a mounting unit connected to said rigid body below said protrusion, wherein said mounting unit is adapted to be attached to said external surface thereby spacing at least said middle portion of said rigid body from said external surface.

2. The apparatus of claim 1, wherein:
    said mounting unit is connected to said middle portion of said rigid body.

3. The apparatus of claim 1, wherein:
    said mounting unit has a mounting unit surface area and a mounting unit width approximately perpendicular thereto;
    said mounting unit surface area is aligned adjacent a body mounting surface area on said rigid body; and said mounting unit width separates said rigid body from said external surface.

4. The apparatus of claim 1, wherein said mounting unit connects to said rigid body at said protrusion.

5. The apparatus of claim 1, further comprising:
a rigid body surface area defined by a rigid body height and a rigid body width, wherein said rigid body surface area is substantially vertical, and wherein said rigid body surface area includes a top portion surface area of said top portion, a middle portion surface area of said middle portion, and a bottom surface area of said bottom portion.

6. The apparatus of claim 5, further comprising:
a top portion depth perpendicular to said rigid body surface area; and
a bottom portion depth perpendicular to said rigid body surface area;
wherein said top portion depth is greater than said bottom portion depth.

7. The apparatus of claim 1, said mounting unit further comprising:
a detachable connector.

8. A method, said method comprising:
obtaining a specimen collection device, said specimen collection device comprising:
a rigid body, said rigid body comprising:
a top portion, wherein said top portion has a holding component for holding a top portion of a specimen bag such that said specimen bag is in an open configuration;
a middle portion connected to said top portion;
a protrusion extending from said middle portion in a first direction; and
a bottom portion connected to said top portion via said middle portion;
a stabilizing unit connected to said rigid body for supporting a bottom portion of said specimen bag and a weight of contents of said specimen bag, wherein said stabilizing unit extends away from said rigid body in a second direction, wherein said second direction is opposite said first direction, and wherein said rigid body and said stabilizing unit are of a contiguous material; and
a mounting unit connected to said rigid body below said protrusion, wherein said mounting unit is adapted to be attached to said external surface thereby spacing at least said middle portion of said rigid body from said external surface; and
attaching a specimen receptacle to said specimen collection device; and
depositing a specimen into said specimen receptacle.

9. The method of claim 8, wherein:
said mounting unit is connected to said middle portion of said rigid body.

10. The method of claim 8, wherein:
said mounting unit has a mounting unit surface area and a mounting unit width approximately perpendicular thereto;
said mounting unit surface area is aligned adjacent a body mounting surface area on said rigid body; and
said mounting unit width separates said rigid body from an external surface.

11. The method of claim 8, wherein said mounting unit connects to said rigid body at said protrusion.

12. The method of claim 8, said specimen collection device further comprising:
a rigid body surface area defined by a rigid body height and a rigid body width, wherein said rigid body surface area is substantially vertical, and wherein said rigid body surface area includes a top portion surface area of said top portion, a middle portion surface area of said middle portion, and a bottom surface area of said bottom portion.

13. The method of claim 12, said specimen collection device further comprising:
a top portion depth perpendicular to said rigid body surface area; and
a bottom portion depth perpendicular to said rigid body surface area;
wherein said top portion depth is greater than said bottom portion depth.

14. The method of claim 8, said mounting unit further comprising:
a detachable connector.

* * * * *